United States Patent
Itoh et al.

(10) Patent No.: US 9,360,409 B2
(45) Date of Patent: Jun. 7, 2016

(54) METHOD FOR MEASURING VISCOELASTIC MODULUS OF SUBSTANCE, AND APPARATUS FOR MEASURING VISCOELASTIC MODULUS OF SUBSTANCE

(75) Inventors: Atsushi Itoh, Chigasaki (JP); Motoko Ichihashi, Chigasaki (JP)

(73) Assignee: ULVAC, INC., Chigasaki-shi (JP)

( * ) Notice: Subject to any disclaimer, the term of this patent is extended or adjusted under 35 U.S.C. 154(b) by 493 days.

(21) Appl. No.: 13/879,704

(22) PCT Filed: Oct. 18, 2011

(86) PCT No.: PCT/JP2011/005810
§ 371 (c)(1),
(2), (4) Date: Apr. 16, 2013

(87) PCT Pub. No.: WO2012/053189
PCT Pub. Date: Apr. 26, 2012

(65) Prior Publication Data
US 2013/0211748 A1    Aug. 15, 2013

(30) Foreign Application Priority Data
Oct. 20, 2010    (JP) ................................. 2010-235657

(51) Int. Cl.
*G01N 29/036*    (2006.01)
*G01N 11/16*    (2006.01)
(Continued)

(52) U.S. Cl.
CPC .................. *G01N 11/16* (2013.01); *G01N 5/02* (2013.01); *G01N 29/022* (2013.01);
(Continued)

(58) Field of Classification Search
CPC . G01N 29/036; G01N 29/041; G01N 29/022; G01H 13/00; G01H 15/00
See application file for complete search history.

(56) References Cited

U.S. PATENT DOCUMENTS

2004/0150428 A1    8/2004    Itoh
2009/0038859 A1    2/2009    Itoh

FOREIGN PATENT DOCUMENTS

EP            1898203 A1    3/2008
JP    2003-315235 A1    11/2003
(Continued)

OTHER PUBLICATIONS

Voinova et al., On Dissipation of Quartz Crystal Microbalance as a Mechanical Spectroscopy Tool, 2004, Spectroscopy 18, pp. 537-544.*

(Continued)

*Primary Examiner* — Toan Le
(74) *Attorney, Agent, or Firm* — Kratz, Quintos & Hanson, LLP (57) ABSTRACT

[Problem] A method for measuring a viscoelastic modulus of a substance and an apparatus for measuring the viscoelastic modulus of the substance are provided for allowing information on viscoelasticity of an adsorption substance to be expressed by moduli G' and G" which are generally used when expressing viscoelasticity, and for further allowing calculation of the viscoelastic modulus in real time.

[Solution] In a system for forming a film by adsorbing a substance to the surface of a piezoelectric element or to a film fixed onto the piezoelectric element in a solution, at least two of N-th waves of the piezoelectric element are used, and at least two of a resonance frequency $F_s$, and half-value frequencies $F_1$ and $F_2$ ($F_2 > F_1$) having half conductance values of a conductance value of the resonance frequency in each N-th wave are used to calculate a mass load term, a viscoelastic term (1), a viscoelastic term (2), and a viscoelastic term (3), and to calculate viscoelastic moduli G' (storage elastic modulus) and G" (loss elastic modulus) of the film.

5 Claims, 3 Drawing Sheets

(51) Int. Cl.
*G01N 5/02* (2006.01)
*G06F 17/13* (2006.01)
*G01N 29/02* (2006.01)

(52) U.S. Cl.
CPC ............ *G01N 29/036* (2013.01); *G06F 17/13* (2013.01); *G01N 2203/0094* (2013.01); *G01N 2291/0256* (2013.01); *G01N 2291/02827* (2013.01); *G01N 2291/0423* (2013.01); *G01N 2291/0426* (2013.01); *G01N 2291/0427* (2013.01)

(56) References Cited

FOREIGN PATENT DOCUMENTS

| JP | 2004-325257 A1 | 11/2004 |
| JP | 2007-10519 A1 | 1/2007 |

OTHER PUBLICATIONS

International Search Report for International Application No. PCT/JP2011/005810 dated Jan. 10, 2012.

First Office Action issued May 26, 2014 by The State Intellectual Property Office of the People's Republic of China in counterpart application No. 201180044927.X with Japanese translation and partial English translation.

Xiao-Ian Wei et al.: "Analysis of the Response Mechanism of Cell Adhesion on Piezoelectric Sensor", ACTA Biophysica Sinica, vol. 22 dated Jun. 30, 2006.

* cited by examiner

METHOD FOR MEASURING VISCOELASTIC MODULUS OF SUBSTANCE, AND APPARATUS FOR MEASURING VISCOELASTIC MODULUS OF SUBSTANCE

TECHNICAL FIELD

The present invention relates to a method for measuring a viscoelastic modulus of a substance and an apparatus for measuring a viscoelastic modulus of a substance, using a sensor for adsorption measurement and physical property evaluation of a substance in a solution in the field of chemistry, physics, biochemistry, pharmacy, material, or the like.

BACKGROUND ART

A relationship between frequency changes and mass loads caused by adsorption of a Quartz Crystal Microbalance (QCM) is expressed by Sauerbrey equation indicated by the following equation 14.

$$\Delta F_s = -\frac{2Nf_0^2}{\sqrt{\rho_Q \mu_Q}} \frac{\Delta m}{A} \qquad \text{Equation 14}$$

However, in the case of measurement in the field of chemistry, biochemistry, pharmacy, or the like in which the measurement is mainly made in a solution, since the solution is contained in an adsorption substance unlike in the atmosphere, the adsorption substance is known to be a film with viscoelastic properties. A frequency change of a resonance frequency $F_s$ measured in conventional QCM has therefore indicated a value that includes a mass load due to adsorption, a viscous load of the solution, and a viscoelastic effect of the adsorption substance itself, and these three elements could not be separated.

Accordingly, the present applicant found from the invention described in Patent Document 1 that the three elements included in a frequency variation of the above $F_s$ can be separated and respectively calculated as frequency variations.

However, even if conversion into mass can be made using the above Sauerbrey equation from a frequency change calculated by a separated mass load, a viscoelastic modulus of an adsorption substance cannot be calculated from a separated viscoelastic element.

Specifically, it was found from the invention described in Patent Document 1 that the three elements included in a frequency variation of the above $F_s$ can be separated and respectively calculated as frequency variations. However, the mutual separation of a mass load term, a viscous load term, and a viscoelastic term cannot be made in all of measurements, and there was a case that a calculated viscous change term was not zero even if there was no viscous change. Furthermore, each separated term was a value of a frequency, and a viscoelastic modulus could not be calculated.

CITATION LIST

Patent Documents

Patent Document 1: JP-A-2007-10519

SUMMARY OF THE INVENTION

Problems to be Solved by the Invention

Accordingly, an object of the present invention is to provide a method for measuring a viscoelastic modulus of a substance that allows information on viscoelasticity of an adsorption substance to be expressed by moduli G' and G" which are generally used when expressing viscoelasticity, and further allows calculation of the viscoelastic modulus in real time. The present invention also has an object to calculate the viscoelasticity loss coefficient, rigidity coefficient, and viscosity coefficient of the adsorption substance from the obtained viscoelastic modulus.

Means of Solving the Problems

In order to solve the above problems, a first solution means in the present invention is characterized in that, in a system for forming a film by adsorbing a substance to the surface of a piezoelectric element or to a film fixed onto the piezoelectric element in a solution, using a sensor with the piezoelectric element submerged on both sides or one side in the solution, at least two of N-th waves (N=1, 3, 5 ... (N=2n+1)) of the piezoelectric element are used, and further at least two of a resonance frequency $F_s$, and half-value frequencies $F_1$ and $F_2$ ($F_2 > F_1$) having half conductance values of a conductance value of the resonance frequency in each N-th wave are used to calculate a mass load term, a viscoelastic term (1), a viscoelastic term (2), and a viscoelastic term (3) represented by the following equations 1 to 3:

$$\Delta F_2 = -\frac{f_0}{\pi z_q}\omega\rho_1 h_1 + \frac{f_0}{\pi z_q}\frac{(G'+G'')}{|G|^2}\omega^2\rho_2\eta_2 h_1 \qquad \text{Equation 1}$$

$$\underbrace{\phantom{XXXXX}}_{\text{Mass load}} \underbrace{\phantom{XXXXXXXXX}}_{\text{Viscoelastic term (1)}}$$

$$\Delta F_w = -\frac{f_0}{\pi z_q}\frac{G'}{|G|^2}\omega^2\rho_2\eta_2 h_1 \qquad \text{Equation 2}$$

$$\underbrace{\phantom{XXXXXXXXX}}_{\text{Viscoelastic term (2)}}$$

$$\Delta F_s = -\frac{f_0}{\pi z_q}\omega\rho_1 h_1 + \frac{f_0}{\pi z_q}\frac{G''}{|G|^2}\omega^2\rho_2\eta_2 h_1 \qquad \text{Equation 3}$$

$$\underbrace{\phantom{XXXXX}}_{\text{Mass load}} \underbrace{\phantom{XXXXXXXXX}}_{\text{Viscoelastic term (3)}}$$

Viscoelastic moduli G' (storage elastic modulus) and G" (loss elastic modulus) of the film are calculated by the following equation 4 and a relational expression G"=C*G', $$G' = \frac{\omega \cdot [\text{mass load}]}{[\text{viscoelastic term (2)}]} \cdot \frac{\rho_2 \eta_2}{(1+C^2)\cdot \rho_1} \qquad \text{Equation 4}$$

wherein $\Delta F_n = \Delta(F_1-F_2)/2$, G is a complex elastic modulus (MPa), G' is a storage elastic modulus (dynamic elastic modulus) (MPa), G" is a loss elastic modulus (dynamic loss) (MPa), ω is an angular frequency, $\rho_2$ is the density (g/cm$^3$) of the solution, $\eta_2$ is the viscosity (Pa s) of the solution, $h_1$ is the thickness (nm) of the formed film, $\rho_1$ is the density (g/cm$^3$) of the formed film, $f_3$ is a fundamental frequency (Hz), and $Z_q$ is the shear mode acoustic impedance (gm/sec/cm$^2$) of crystal.

A second solution means in the present invention is characterized in that the viscoelasticity loss coefficient tanδ of the adsorbed substance, the rigidity coefficient μ of the adsorption substance, and the viscosity coefficient η of the adsorbed substance are calculated using the viscoelastic modulus G' in the first solution means.

A third solution means in the present invention is characterized in that the viscoelastic modulus, the loss coefficient, the rigidity coefficient, or the viscosity coefficient of the adsorption substance are calculated along with the measurement of the frequency variation in the first solution means.

A fourth solution means in the present invention is characterized in that the piezoelectric element is a quartz crystal oscillator, an APM (acoustic plate mode sensor), an FPW (flexural plate-wave sensor), or a SAW (sourface acoustic-wave sensor) in the first solution means.

A measuring apparatus in the present invention, which is an apparatus for measuring the viscoelastic modulus of the substance in a system for forming a film by adsorbing a substance to the surface of a piezoelectric element or to a film fixed onto the piezoelectric element in a solution, using a sensor with the piezoelectric element submerged on both sides or one side in the solution, includes a measuring means for measuring at least two of a resonance frequency $F_s$, and half-value frequencies $F_1$ and $F_2$ ($F_2 > F_1$) having half conductance values of a conductance value of the resonance frequency in the piezoelectric element, and includes an arithmetic means for using the values measured by the measuring means to calculate a mass load term, a viscoelastic term (1), a viscoelastic term (2), and a viscoelastic term (3) represented by the following equations 1 to 3:

$$\Delta F_2 = -\underbrace{\frac{f_0}{\pi z_q}\omega\rho_1 h_1}_{\text{Mass load}} + \underbrace{\frac{f_0}{\pi z_q}\frac{(G'+G'')}{|G|^2}\omega^2\rho_2\eta_2 h_1}_{\text{Viscoelastic term}(1)} \quad \text{Equation 1}$$

$$\Delta F_w = -\underbrace{\frac{f_0}{\pi z_q}\frac{G'}{|G|^2}\omega^2\rho_2\eta_2 h_1}_{\text{Viscoelastic term}(2)} \quad \text{Equation 2}$$

$$\Delta F_s = -\underbrace{\frac{f_0}{\pi z_q}\omega\rho_1 h_1}_{\text{Mass load}} + \underbrace{\frac{f_0}{\pi z_q}\frac{G''}{|G|^2}\omega^2\rho_2\eta_2 h_1}_{\text{Viscoelastic term}(3)} \quad \text{Equation 3}$$

and further to calculate viscoelastic moduli G' (storage elastic modulus) and G" (loss elastic modulus) of the film by the following equation 4 and a relational expression G"=C*G', $$G' = \frac{\omega \cdot [\text{mass load}]}{[\text{viscoelastic term}(2)]} \cdot \frac{\rho_2\eta_2}{(1+C^2)\cdot\rho_1} \quad \text{Equation 4}$$

wherein $\Delta F_s = \Delta(F_1-F_2)/2$, G is a complex elastic modulus (MPa), G' is a storage elastic modulus (dynamic elastic modulus) (MPa), G" is a loss elastic modulus (dynamic loss) (MPa), $\omega$ is an angular frequency, $\rho_2$ is the density (g/cm$^3$) of the solution, $\eta_2$ is the viscosity (Pa s) of the solution, $h_1$ is the thickness (nm) of the formed film, $\rho_1$ is the density (g/cm$^3$) of the formed film, $f_0$ is a fundamental frequency (Hz), and $Z_q$ is the shear mode acoustic impedance (gm/sec/cm$^2$) of crystal.

Effects of the Invention

Accurate information on viscoelasticity has not been conventionally obtained because of attaining the measurement of only the resonance frequency $F_s$ including an element of a mass load due to adsorption and an element of viscoelasticity of an adsorption substance. Further, although elements of mass, viscosity, and viscoelasticity could be separately obtained by the invention proposed in Patent Document 1, they could be only represented as frequency variations.

However, the present invention attained a method for calculating general G' and G" values as parameters representing viscoelasticity from the obtained frequency variations of the respective elements. Consequently, viscoelastic moduli G' and G" can be obtained in real time during the measurement of the frequency variations, and physical information (a loss coefficient, an elasticity coefficient, and a viscosity coefficient) other than the frequencies can be acquired in an instant. A more accurate physical property evaluation of the adsorption substance can thereby be made.

DESCRIPTION OF REFERENCE NUMERAL

1 Cell
2 Measuring means (network analyzer)
3 Control means
4 Temperature control means
5 Temperature regulating means
6 First arithmetic part
7 Second arithmetic part
8 Display part

MODE FOR CARRYING OUT THE INVENTION

The measurement principle of the present invention is explained as follows.

The change of impedance Z in the case of adsorbing a viscoelastic film to a quartz crystal oscillator in a solution by a transmission theory of Martin et al. (V. E. Granstaff, S. J. Martin, J. Appl. Phys. 1994, 75, 1319) is expressed by the following equation (1).

Equation 5

$$Z = (\omega\rho_2\eta_2/2)^{1/2}(1+j)j\omega\rho_1 h_1 + \frac{(G'-jG'')}{|G|^2}\omega^2\rho_2\eta_2 h_1 \quad (1)$$

From the equation (1), the change of a resonance frequency $F_s$ is expressed by the equation (2), and the variation of half ($F_1-F_2$)/2 (=$F_w$) of a half-value frequency is expressed by the equation (3).

Equation 6

$$\Delta Fs = \text{Im}(Z) = -\frac{f_0}{\pi z_q}(\omega \rho_2 \eta_2/2)^{1/2} - \frac{f_0}{\pi z_q}\omega \rho_1 h_1 + \frac{f_0}{\pi z_q}\frac{G''}{|G|^2}\omega^2 \rho_2 \eta_2 h_1 \quad (2)$$

Equation 7

$$\Delta\frac{(F_1-F_2)}{2} = \Delta Fw = \text{Re}(Z) = -\frac{f_0}{\pi z_q}(\omega \rho_2 \eta_2/2)^{1/2} - \frac{f_0}{\pi z_q}\frac{G'}{|G|^2}\omega^2 \rho_2 \eta_2 h_1 \quad (3)$$

From the equations (2) and (3), the variation of a frequency $F_2$ can be obtained as shown in the equation (4).

Equation 8

$$\Delta F_2 = -\frac{f_0}{\pi z_q}\omega \rho_1 h_1 + \frac{f_0}{\pi z_q}\frac{(G'-G'')}{|G|^2}\omega^2 \rho_2 \eta_2 h_1 \quad (4)$$

In this specification, G is a complex elastic modulus (MPa), G' is a storage elastic modulus (dynamic elastic modulus) (MPa), G" is a loss elastic modulus (dynamic loss) (MPa), $\omega$ is an angular frequency, $\rho_2$ is the density (g/cm$^3$) of the solution, $\eta_2$ is the viscosity (Pa s) of the solution, $h_1$ is the thickness (nm) of the formed film, $\rho_1$ is the density (g/cm$^3$) of the formed film, $\eta_1$ is a viscosity coefficient (Pa s) of the formed film, $f_0$ is a fundamental frequency (Hz), and $Z_q$ is the shear mode acoustic impedance (gm/sec/cm$^2$) of crystal.

A Voight model frequently used as a viscoelasticity model of a film is applied to G' and G".

A model in which a spring G of an elastic element and a dashpot $\eta$ are connected in parallel is expressed by the following expression:

$$G = G'+jG'' = \mu+j\omega\eta$$

Herein, in the case of $\omega\eta = C\mu$ (C: constant, $\mu$: rigidity coefficient (MPa)), the equation (2) can be transformed as follows:

$$\Delta Fw = -\frac{f_0}{\pi z_q}\frac{G'}{|G|^2}\omega^2 \rho_2 \eta_2 h_1 \quad \text{Equation 9}$$

$$= -\frac{f_0}{\pi z_q}\frac{\mu}{(\mu_1^2+\omega^2\eta_1^2)}\omega^2 \rho_2 \eta_2 h_1$$

In the case of a N-th wave, the equation is as follows:

$$\Delta Fw_N = -\frac{f_0}{\pi z_q}\frac{1}{(1+C^2N^2)}\frac{N^2\omega^2\rho_2\eta_2 h_1}{\mu_1} \quad \text{Equation 10}$$

An equation including a constant C is obtained by making division of respective $\Delta F_w$ values of two frequencies.

$$\frac{\Delta Fw_3}{\Delta Fw_1} = A = \frac{-\frac{1}{(1+9C^2)}\frac{9\omega^2\rho_2\eta_2 h_1}{\mu_1}}{-\frac{1}{(1+C^2)}\frac{\omega^2\rho_2\eta_2 h_1}{\mu_1}} = \frac{9(1+C^2)}{1+9C^2} \quad \text{Equation 11}$$

The above equation is an equation in the case of using the frequency variation $F_w$ of a fundamental wave (N=1) and a threefold wave (N=3).

A value obtained by dividing the frequency variation $F_{w3}$ obtained by measurement, by $F_{w1}$ is made A, and the value A is substituted in the left side of the above equation to calculate the following constant C.

$$C = \frac{1}{3}*\sqrt{\frac{9-A}{A-1}} \quad \text{Equation 12}$$

The frequency changes of the respective terms indicated in the following equations 1 to 3 are obtained from the calculated value C and the measured frequency variations $\Delta F_2$, $\Delta F_w$, and $\Delta F_s$ values of the fundamental wave. This measurement is made on condition that there is no occurrence of the viscous load of the solution.

The change of the viscous load occurs when a buffer solution and a sample solution greatly differ in viscosity, for example, when a sample containing a glycerol solution of high concentration is added to the buffer solution for measurement. In most cases, the sample solution and the buffer solution are almost equal in viscosity, and it is therefore considered that no viscous change occurs.

$$\Delta F_2 = -\frac{f_0}{\pi z_q}\omega\rho_1 h_1 + \frac{f_0}{\pi z_q}\frac{(G'+G'')}{|G|^2}\omega^2\rho_2\eta_2 h_1 \quad \text{Equation 1}$$

Mass load   Viscoelastic term (1)

$$\Delta Fw = -\frac{f_0}{\pi z_q}\frac{G'}{|G|^2}\omega^2\rho_2\eta_2 h_1 \quad \text{Equation 2}$$

Viscoelastic term (2)

$$\Delta Fs = -\frac{f_0}{\pi z_q}\omega\rho_1 h_1 + \frac{f_0}{\pi z_q}\frac{G''}{|G|^2}\omega^2\rho_2\eta_2 h_1 \quad \text{Equation 3}$$

Mass load   Viscoelastic term (3)

First, since $\Delta F_w$ is established only with the viscoelastic term (2),

Viscoelastic term (2)=$\Delta F_w$ is satisfied.

Secondly, the viscoelastic term (1) is obtained by the following expression. Since the constant C can be expressed by G"/G', C=G"/G' is substituted and multiplied by the viscoelastic term (2) to calculate the viscoelastic term (1).

Viscoelastic term (1)=−(1+C)*Viscoelastic term (2)

The mass load term is obtained by substituting the obtained value of the viscoelastic term (1) in an expression of $\Delta F_2$.

Mass load term=$\Delta F_2$−Viscoelastic term (1)

Finally, the viscoelastic term (3) is obtained by substituting the obtained value of the mass load term in an expression of $\Delta F_s$.

Viscoelastic term (3)=$\Delta F_s$−Mass load term

On this principle, it is proved that the respective terms can be separated as the frequency variations.

Further, the obtained frequency variations of the mass load term and the viscoelastic term (2) are used to calculate the viscoelastic moduli G' and G" by the following equation, wherein ω is an angular frequency, $\rho_2$ is the density (g/cm³) of a solution, $\eta_2$ is the viscosity (Pa s) of a solution, and pi is the density (g/cm³) of a film.

$$G' = \frac{\omega \cdot [\text{mass load}]}{[\text{viscoelastic term}(2)]} \cdot \frac{\rho_2 \eta_2}{(1+C^2) \cdot \rho_1} \qquad \text{Equation 4}$$

The constant C also corresponds to a loss coefficient tans (=G"/G') representing a loss portion of a viscoelastic body. The loss coefficient is one of the parameters indicating the hardness of the viscoelastic body by indicating an ideal solid when the loss coefficient is 0 and indicating an ideal liquid when the loss coefficient is ∞.

Further, since the Voight model $G=G'+jG''=\mu+j\omega\eta$ is applied to the obtained viscoelastic modulus, the rigidity coefficient μ (MPa) and viscosity coefficient η (Pa s) of the adsorption substance can be calculated from the G' and G" values.

The frequencies $F_s$, $F_1$, and $F_2$ used in the above measuring method can be measured by a method based on an oscillating circuit, a method obtained by frequency scanning from external equipment such as an impedance analyzer or a network analyzer, etc., and the measuring method is not limited as long as the resonance frequency $F_s$, and the half-value frequencies $F_1$ and $F_2$ ($F_2>F_1$) having half conductance values of a conductance value of the resonance frequency are measured.

Figure 1:
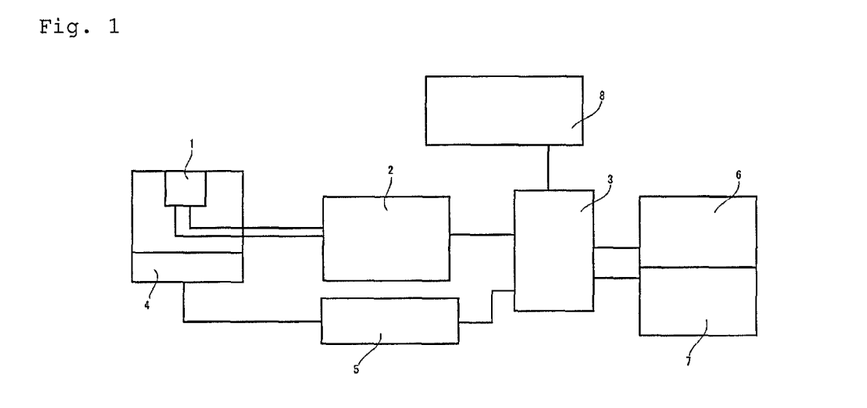
FIG. 1 is an explanatory diagram of apparatus configuration of the embodiment of the present invention.

As shown in FIG. 1, the apparatus of the present invention includes a control means 3 controlling a cell 1 having a piezoelectric element, through a network analyzer 2 which is a measuring means; a first arithmetic part 6 for computing the frequency components of frequencies measured by the network analyzer 2; a second arithmetic part 7 for computing film thickness and viscoelasticity using the result obtained in the first arithmetic part 6; and a display means 8 for alternately or simultaneously displaying the values of the frequencies, viscoelasticity, etc. obtained in the respective arithmetic parts. The control means 3, the arithmetic parts 6, 7, and the display part 8 can be composed of usual personal computers and monitors.

In the example shown in the figure, a temperature control means 4 such as a Peltier element is provided at the lower face of the cell 1 to regulate the temperature of the cell 1, and a temperature regulating means 5 for regulating the temperature control means 4 is controlled in the same way by the control means 3.

Figure 5:
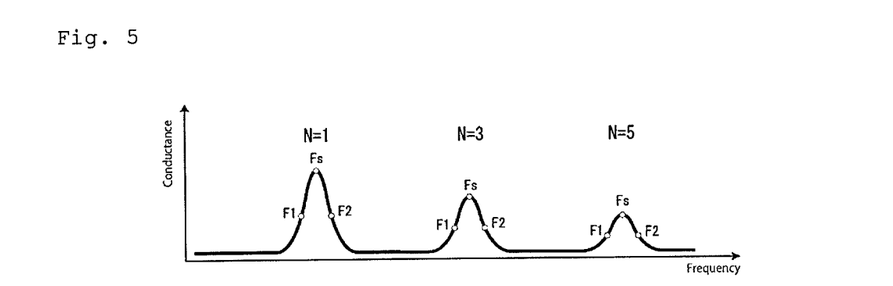
FIG. 5 is an explanatory diagram of the measured frequencies of N-th waves etc. of one embodiment in the present invention.

The fundamental wave and the threefold wave are used in the above explanation. However, the present invention can be used if at least two frequencies are used out of overtone frequencies including the fundamental wave as shown in FIG. 5.

The piezoelectric element used in the present invention is not limited as long as it can measure the target frequencies, and a quartz crystal oscillator, an APM (acoustic plate mode sensor), an FPW (flexural plate-wave sensor), or a SAW (sourface acoustic-wave sensor) can be also used.

EXAMPLES

The obtained result of viscoelastic moduli of a biomolecule film and the like is shown in the following table 1 using the apparatus explained referring to the FIG. 1, and using the fundamental wave and the threefold wave of 27 MHz according to the present invention.

Each sample used in the experiment is as follows.
1) 50 nm beads (the final concentration when measured in latex beads is 10 μg/ml)
2) Neutravidin (the final concentration when measured in globular protein is 10 μg/ml)
3) ssDNA 30 mer (single-stranded DNA with a length of 30 mer, and the final concentration when measured is 1 μg/ml)
4) ssDNA 60 mer (single-stranded DNA with a length of 60 mer, and the final concentration when measured is 1 μg/ml)
5) ssDNA 90 mer (single-stranded DNA with a length of 90 mer, and the final concentration when measured is 1 μg/ml)
6) dsDNA 90 mer (double-stranded DNA with a length of 90 mer, and the final concentration when measured is 1 μg/ml)

TABLE 1

|  | G' (Mpa) | G" (Mpa) |
| --- | --- | --- |
| 50 nm beads | 2.090 | 1.264 |
| Neutravidin | 1.660 | 1.066 |
| ssDNA 30 mer | 0.360 | 0.315 |
| ssDNA 60 mer | 0.340 | 0.237 |
| ssDNA 90 mer | 0.301 | 0.201 |
| dsDNA 90 mer | 1.790 | 0.443 |

Figure 2:
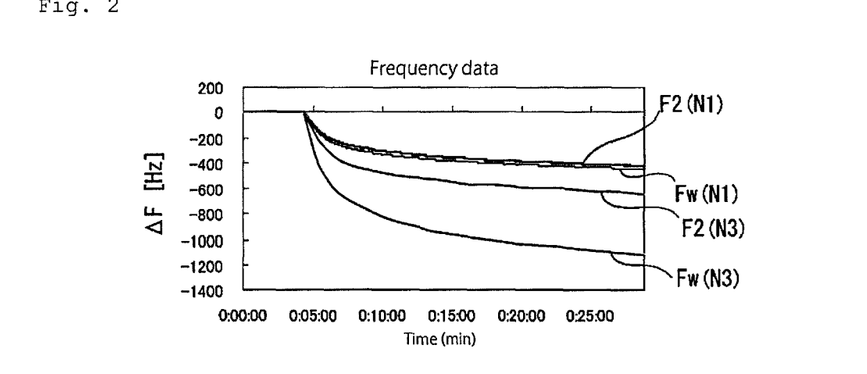
FIG. 2 is a graph showing the measured result of one example of the present invention.
Figure 3:
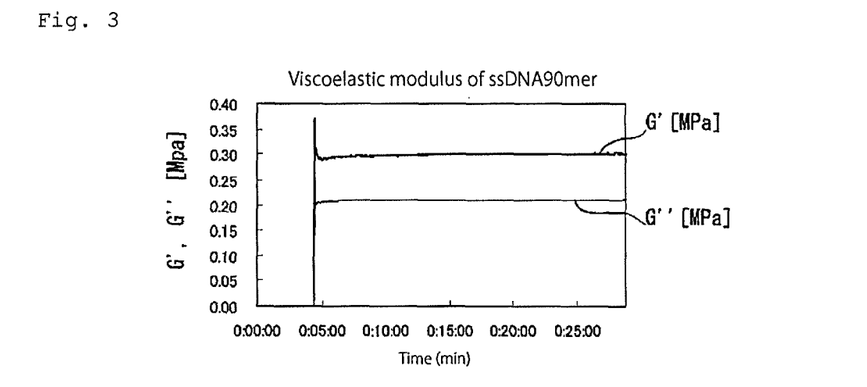
FIG. 3 is a graph showing changes in the value calculated based on the measured result of the same example.
Figure 4:
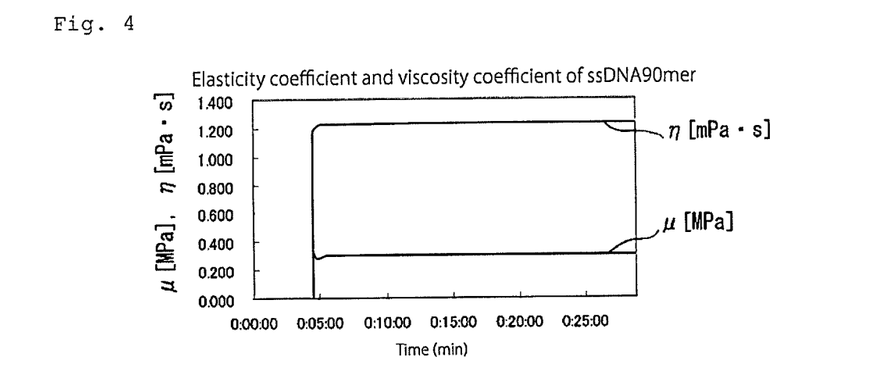
FIG. 4 is a graph showing changes in the viscoelastic coefficient and the viscosity coefficient in the same example.

Next, the measured data of the fundamental wave (N1) and threefold wave (N3) of the ssDNA 90 mer are specifically shown in FIGS. 2 to 4.

The FIG. 2 is a graph showing the measured data of respective $\Delta F_2$ and $\Delta F_w$ of the above two kinds of different frequencies, and a graph in FIG. 3 shows viscoelastic moduli G' and G" of a DNA film calculated in real time from the measured data.

A graph in FIG. 4 shows the result of an elasticity coefficient and a viscosity coefficient of the DNA film obtained in real time in the same way from the viscoelastic moduli obtained in FIG. 3.

From the above result, the viscoelastic moduli G' and G" could be obtained from the frequency variations by the method in the present example, and it was proved that the loss coefficient, the elasticity coefficient, and the viscosity coefficient of the object to be measured can be measured in real time at the time of measurement.

Other examples using the measuring method in the present invention are explained.

Figure 6:
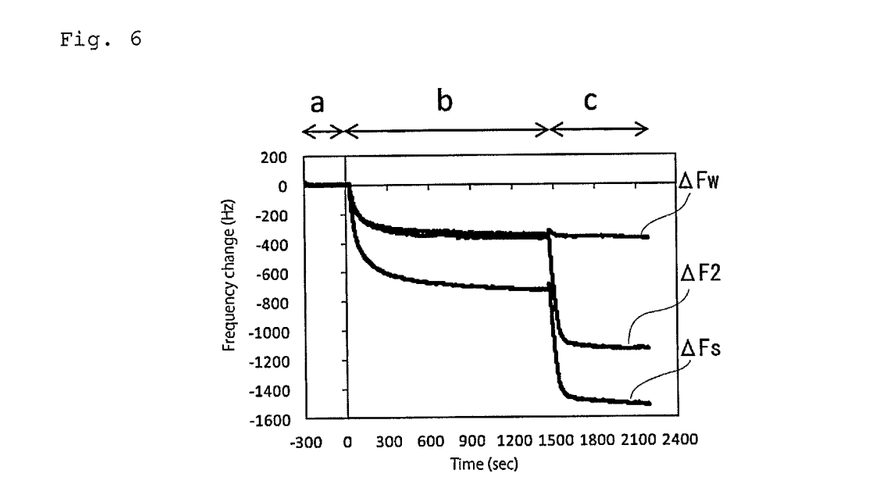
FIG. 6 is a graph showing frequency change values for use in other examples of the present invention.
Figure 7:
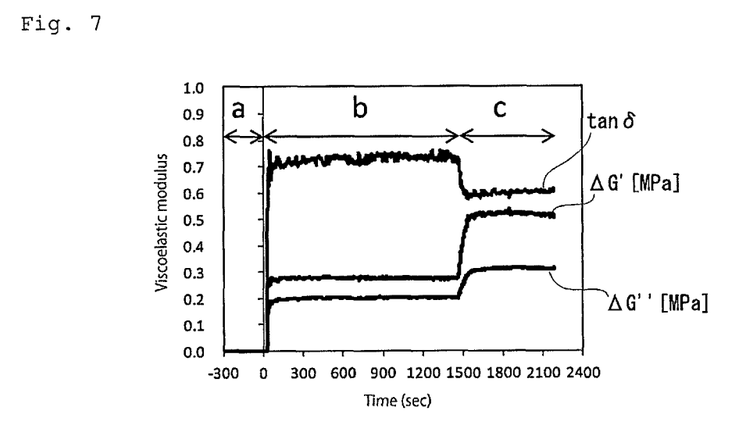
FIG. 7 is a graph showing the result of an analysis made using a measuring method of the present invention using the frequency change values in FIG. 6.
Figure 8:
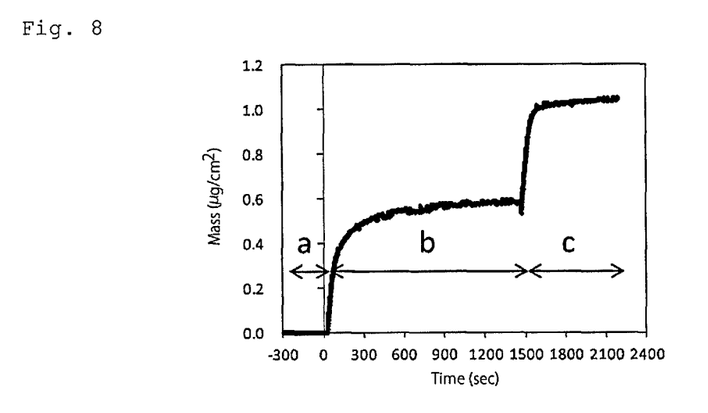
FIG. 8 is a graph showing the result of an analysis made using a measuring method of the present invention using the frequency change values in FIG. 6.

FIG. 6 shows the frequency change values obtained by measurement, and FIGS. 7 and 8 show the result of making an analysis using the measuring method of the present invention with the use of the frequency change values.

In each figure, a to c are as follows:
a. a region for modifying and stabilizing NeutrAvidin (protein) on a gold electrode in a solution
b. a change region when injecting 60 mer biotinylated DNA
c. a change region when injecting 60 mer DNA which is a complementary strand of the above biotinylated DNA to cause hybridization FIGS. 6 to 8 proved the occurrence of an adsorption phenomenon from changes in $\Delta F_s$ and $\Delta F_2$ in the region b or c in FIG. 1 in the conventional QCM measuring method, but the viscoelasticity of the adsorption film cannot be digitized. However, physical property values such as viscoelastic moduli, mass, and film thickness of the film formed on the electrode in the solution can be calculated by the method of the present invention.

The viscoelastic change of a ΔG' value occurring from b to c in FIG. 7 shows an increase in hardness in the DNA film due to the occurrence of hybridization of the single-stranded DNA with the complementary strand. The tans called the loss coefficient shows a value 0 as a complete solid and a value ∞ as a complete solution. However, the film hardness was proved to be increased from the decrease of the tanδ.

Further, FIG. 8 proved that the adsorption of the single-stranded DNA and the adsorption of the complementary strand can be measured by the increase of mass.

The invention claimed is:

1. A method for measuring a viscoelastic modulus of a substance comprising the steps of:
submerging both sides or one side of a sensor with a piezoelectric element in a solution;
adsorbing the substance to a surface of the piezoelectric element or to a film fixed onto the piezoelectric element in the solution;
measuring at least two of a resonance frequency $F_s$, and half-value frequencies $F_1$ and $F_2$ ($F_2 > F_1$) having half conductance values of a conductance value of the resonance frequency in each of at least two of N-th waves (N=1, 3, 5 . . . (N=2n+1)) of the piezoelectric element by a method based on an oscillating circuit or a method obtained from external equipment including an impedance analyzer or a network analyzer; and
executing first to sixth calculation steps by using the values measured in the measuring step to calculate the viscoelastic modulus of the adsorbed substance by an arithmetic means,
wherein the first calculating step is a step calculating a constant C based on an equation obtained by a value obtained by making division of respective $\Delta F_{WN}$ of two N-th waves represented by Equation 1 and a value obtained by making division of respective $\Delta F_{WN}$ of two N-th waves obtained based on the half-value frequencies $F_1$ and $F_2$ obtained in the measuring step, the $\Delta F_{WN}$ being a variation of a half value of a width between half-value frequencies F1 and F2 (=$\Delta(F_1-F_2)/2$), $$\Delta Fw_N = -\frac{f_0}{\pi z_q} \frac{1}{(1+C^2N^2)} \frac{N^2 \omega^2 \rho_2 \eta_2 h_1}{\mu_1} \quad \text{Equation 1}$$

the second calculating step is a step calculating a viscoelastic term (2) by substituting $\Delta F_W$ obtained based on the half-value frequencies $F_1$ and $F_2$ obtained in the measuring step into Equation 2, $$\Delta Fw = -\frac{f_0}{\pi z_q} \frac{G'}{|G|^2} \omega^2 \rho_2 \eta_2 h_1 \quad \text{Equation 2}$$

Viscoelastic term (2)

the third calculating step is a step calculating a viscoelastic term (1) by substituting the viscoelastic term (2) obtained in the second calculating step into Equation 5 obtained by substituting Equation 4 into the viscoelastic term (1) in Equation 3, $$\Delta F_2 = -\frac{f_0}{\pi z_q} \omega \rho_1 h_1 + \frac{f_0}{\pi z_q} \frac{(G'+G'')}{|G|^2} \omega^2 \rho_2 \eta_2 h_1 \quad \text{Equation 3}$$

Mass load    Viscoelastic term (1)

Equation 4

$C = G''/G'$

Equation 5

Viscoelastic term (1)=−(1+C)*Viscoelastic term (2)

the fourth calculating step is a step calculating a mass load in the Equation 3 based on a variation $\Delta F_2$ of the half-value frequency $F_2$ obtained in the measuring step and the viscoelastic term (1) obtained in the third calculating step,
the fifth calculating step is a step calculating a viscoelastic term (3) in Equation 6 based on a variation $\Delta F_s$ of the resonance frequency Fs obtained in the measuring step and the mass load obtained in the fourth calculating step, $$\Delta Fs = -\frac{f_0}{\pi z_q} \omega \rho_1 h_1 + \frac{f_0}{\pi z_q} \frac{G''}{|G|^2} \omega^2 \rho_2 \eta_2 h_1 \quad \text{Equation 6}$$

Mass load    Viscoelastic term (3)

the sixth calculating step is a step calculating the viscoelastic moduli G' (storage elastic modulus) and G" (loss elastic modulus) based on Equation 7 and Equation 4, $$G' = \frac{\omega \cdot [\text{mass load}]}{[\text{viscoelastic term (2)}]} \cdot \frac{\rho_2 \eta_2}{(1+C^2) \cdot \rho_1} \quad \text{Equation 7}$$

wherein $\Delta F_w = \Delta(F_1-F_2)/2$, G is a complex elastic modulus (MPa), G' is a storage elastic modulus (dynamic elastic modulus) (MPa), G" is a loss elastic modulus (dynamic loss) (MPa), ω is an angular frequency, $\rho_2$ is the density (g/cm$^3$) of the solution, $\eta_2$ is the viscosity (Pa s) of the solution, $h_1$ is the thickness (nm) of a film formed by the adsorbed substance, $\rho_1$ is the density (g/cm$^3$) of a film formed by the adsorbed substance, $f_0$ is a fundamental frequency (Hz), $Z_q$ is the shear mode acoustic impedance (gm/sec/cm$^2$) of crystal, and $\mu_1$ is the rigidity coefficient of the adsorbed substance.

2. The method for measuring a viscoelastic modulus of a substance according to claim 1, wherein the viscoelasticity loss coefficient tanδ(=G"/G') of the adsorbed substance, the rigidity coefficient $\mu_1$ of the absorbed substance, and the viscosity coefficient η of the adsorbed substance are calculated using the viscoelastic modulus G'.

3. The method for measuring a viscoelastic modulus of a substance according to claim 1, wherein the viscoelastic modulus, the loss coefficient, the rigidity coefficient, or the viscosity coefficient of the absorbed substance are calculated along with the measurement of the frequency variations.

4. The method for measuring a viscoelastic modulus of a substance according to claim 1, wherein the piezoelectric element is a quartz crystal oscillator, an APM (acoustic plate mode sensor), an FPW (flexural plate-wave sensor), or a SAW (surface acoustic-wave sensor).

5. An apparatus for measuring a viscoelastic modulus of a substance in a system adsorbing the substance to a surface of a piezoelectric element or to a film fixed onto the piezoelectric element in a solution, using a sensor with the piezoelectric element submerged on both sides or one side in the solution, the apparatus comprising:
a measuring means for measuring at least two of a resonance frequency $F_s$, and half-value frequencies $F_1$ and $F_2$ ($F_2 > F_1$) having half conductance values of a conductance value of the resonance frequency each of at least two of N-th waves (N=1, 3, 5 . . . (N=2n+1)) of in the piezoelectric element by a method based on an oscillating circuit or a method obtained from external equipment including an impedance analyzer or a network analyzer; and an arithmetic means for executing first to sixth calculations by using the values measured by the measuring means to calculate the viscoelastic modulus, wherein the first calculation is calculating a constant C based on an equation obtained by a value obtained by making division of respective $\Delta F_{WN}$ of two N-th waves represented by Equation 1 and a value obtained by making division of respective $\Delta F_{WN}$ of two N-th waves obtained based on the half-value frequencies $F_1$ and $F_2$ obtained by the measuring means, the $\Delta F_{WN}$ being a variation of a half value of a width between half-value frequencies $F_1$ and $F_2$ ($=\Delta(F_1-F_2)/2$), $$\Delta F w_N = -\frac{f_0}{\pi z_q}\frac{1}{(1+C^2N^2)}\frac{N^2\omega^2\rho_2\eta_2 h_1}{\mu_1} \qquad \text{Equation 1}$$

the second calculation is calculating a viscoelastic term (2) by substituting $\Delta F_W$ obtained based on the half-value frequencies $F_1$ and $F_2$ obtained by the measuring means into Equation 2, $$\Delta F w = -\frac{f_0}{\pi z_q}\frac{G'}{|G|^2}\omega^2\rho_2\eta_2 h_1 \qquad \text{Equation 2}$$

Viscoelastic term (2)

the third calculation is calculating a viscoelastic term (1) by substituting the viscoelastic term (2) obtained by the second calculation into Equation 5 obtained by substituting Equation 4 into the viscoelastic term (1) in Equation 3, $$\Delta F_2 = -\frac{f_0}{\pi z_q}\omega\rho_1 h_1 + \frac{f_0}{\pi z_q}\frac{(G'+G'')}{|G|^2}\omega^2\rho_2\eta_2 h_1 \qquad \text{Equation 3}$$

Mass load   Viscoelastic term (1)

Equation 4

$$C = G''/G'$$

Equation 5

Viscoelastic term (1)=−(1+C)*Viscoelastic term (2)

the fourth calculation is calculating a mass load in Equation 3 based on a variation $\Delta F_2$ of the half-value frequency $F_2$ obtained by the measuring means and the viscoelastic term (1) obtained by the third calculation, the fifth calculation is calculating a viscoelastic term (3) in Equation 6 based on a variation $\Delta F_S$ of the resonance frequency $F_S$ obtained by the measuring means and the mass load obtained by the fourth calculation, $$\Delta F s = -\frac{f_0}{\pi z_q}\omega\rho_1 h_1 + \frac{f_0}{\pi z_q}\frac{G''}{|G|^2}\omega^2\rho_2\eta_2 h_1 \qquad \text{Equation 6}$$

Mass load   Viscoelastic term (3)

the sixth calculation is calculating the viscoelastic moduli G' (storage elastic modulus) and G" (loss elastic modulus) based on Equation 7 and Equation 4, $$G' = \frac{\omega\cdot[\text{mass load}]}{[\text{viscoelastic term (2)}]}\cdot\frac{\rho_2\eta_2}{(1+C^2)\cdot\rho_1} \qquad \text{Equation 7}$$

wherein $\Delta F_W = \Delta(F_1-F_2)/2$, G is a complex elastic modulus (MPa), G' is a storage elastic modulus (dynamic elastic modulus) (MPa), G" is a loss elastic modulus (dynamic loss) (MPa), $\omega$ is an angular frequency, $\rho_2$ is the density (g/cm$^3$) of the solution, $\eta_2$ is the viscosity (Pa s) of the solution, $h_1$ is the thickness (nm) of a film formed by the adsorbed substance, $\rho_1$ is the density (g/cm$^3$) of a film formed by the adsorbed substance, $f_0$ is a fundamental frequency (Hz), and $Z_q$ is the shear mode acoustic impedance (gm/sec/cm$^2$) of crystal, and $\mu_1$ is the rigidity coefficient of the adsorbed substance.

\* \* \* \* \*